(12) United States Patent
Wynn et al.

(10) Patent No.: US 8,935,960 B2
(45) Date of Patent: Jan. 20, 2015

(54) METHOD AND KIT FOR STAND-OFF DETECTION OF EXPLOSIVES

(75) Inventors: Charles M. Wynn, Groton, MA (US); Robert W. Haupt, Lexington, MA (US); Sumanth Kaushik, Belmont, MA (US); Stephen T. Palmacci, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 850 days.

(21) Appl. No.: 13/010,333

(22) Filed: Jan. 20, 2011

(65) Prior Publication Data

US 2012/0186352 A1    Jul. 26, 2012

(51) Int. Cl.
*G01N 33/22*    (2006.01)
*G01N 21/17*    (2006.01)

(52) U.S. Cl.
CPC .......... *G01N 21/1702* (2013.01); *G01N 33/227* (2013.01); *G01N 33/22* (2013.01)
USPC .......... 73/655; 73/24.02; 73/24.06; 340/600; 250/338.5; 250/338.3; 250/341.1

(58) Field of Classification Search
CPC . G01N 21/1702; G01N 33/22; G01N 33/227; G01N 2021/1704; G01N 2021/1706; G01N 2021/1708
USPC .......... 73/24.01, 24.02, 24.06, 655; 340/600; 250/338.5
See application file for complete search history.

(56) References Cited

U.S. PATENT DOCUMENTS

| | | | |
|---|---|---|---|
| 5,760,898 A | 6/1998 | Haley et al. | |
| 6,797,944 B2 | 9/2004 | Nguyen et al. | |
| 7,089,796 B2 * | 8/2006 | Pepper et al. | 73/602 |
| 7,644,606 B2 * | 1/2010 | Sheen et al. | 73/24.02 |
| 7,961,313 B2 * | 6/2011 | Van Neste et al. | 356/311 |
| 8,148,689 B1 * | 4/2012 | Braunheim | 250/339.07 |
| 2006/0278069 A1 * | 12/2006 | Ryan | 86/50 |
| 2009/0090187 A1 * | 4/2009 | Sano | 73/655 |

FOREIGN PATENT DOCUMENTS

FR    2415792 A * 9/1979

OTHER PUBLICATIONS

"Optics & Infrared Sensing: Differential Remote Photoacoustic Spectroscopy (DIRPAS)," http://infrared.pnl.gov/integration/'dirpas.asp, last updated on Mar. 2009.
MicroSpart, "Explosive Trace Detection," www.mofet.org.il (2010).
Brown, C.G., et al., "Remote Femtosecond Laser Induced Breakdown Spectroscopy (LIBS) in a Standoff Detection Regime."
(Continued)

*Primary Examiner* — Peter Macchiarolo
*Assistant Examiner* — Rose M Miller
(74) *Attorney, Agent, or Firm* — Hamilton, Brook, Smith & Reynolds, P.C.

(57) ABSTRACT

A kit for detecting the presence of an explosive includes a pulsed focused energy source located at a target distance away from a substrate, the energy having a magnitude sufficient to release the internal energy of an explosive if present on the substrate and thereby generate an acoustic wave. The kit also includes a detector adapted to detect the acoustic wave at a detection distance away from the substrate.

19 Claims, 8 Drawing Sheets

(56) References Cited

OTHER PUBLICATIONS

Clough, et al., "Laser Induced Photoacoustics Influenced By Single-Cycle Terahertz Radiation," *Optics Letters*, 35(21): 3544-3546 (2010).

Haupt, R. W., and Rolt, K. D. "Standoff Acoustic Laser Technique to Locate Buried Land Mines."

Van Neste, C. W. et al., "Standoff Photoacoustic Spectroscopy," *Applied Physics Letters*, 92: 234102-234103 (2008).

Wynn, C. M., et al., "Detection of Condensed-Phase Explosives Via Laser-Induced Vaporization, photodissociation, and resonant excitation," *Applied Optics*, 47(31): 5767-5776 (2008).

Wynn, C.M. et al., "Noncontact detection of homemade Explosive Constituents via Photodissocation Followed by Laser-induced fluorescence," *Optics Express*, 18(6): 5399-5406 (2010).

Notification of Transmittal of the International Search Report and The Written Opinion of the International Searching Authority, or the Declaration for PCT/US2012/021974, mailed on May 29, 2012.

International Preliminary Report on Patentability for International Application No. PCT/US2012/021974, Date of Mailing Aug. 1, 2013, "Method And Kit For Stand-Off Detection Of Explosives," 9 pages.

Tam, A.C., "Applications of Photoacoustic Sensing Techniques", Reviews of Modern Physics, vol. 58, No. 2, Apr. 1986.

* cited by examiner

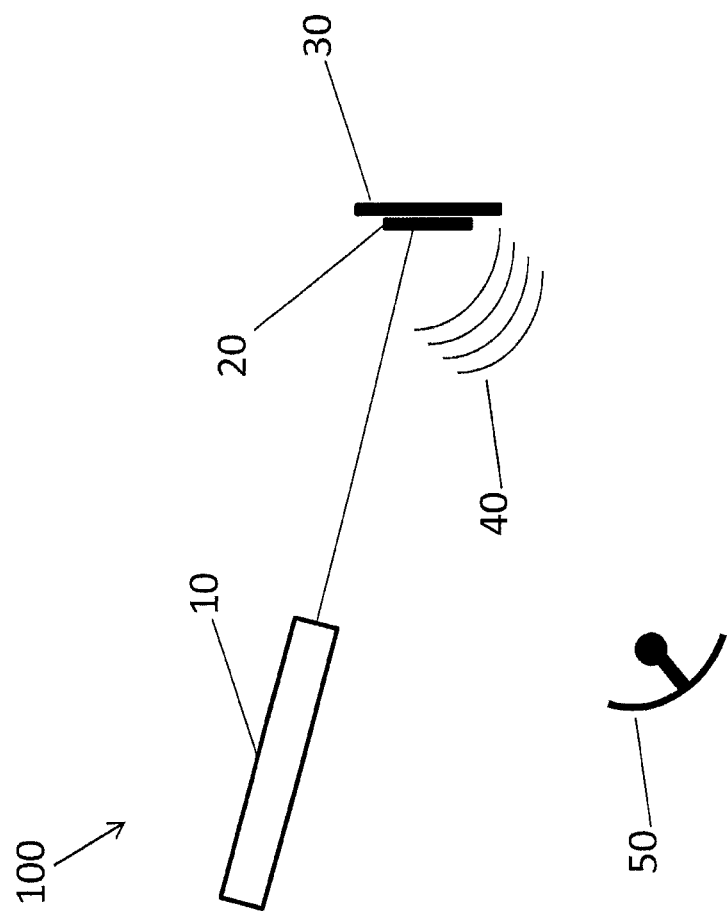

US 8,935,960 B2

METHOD AND KIT FOR STAND-OFF DETECTION OF EXPLOSIVES

GOVERNMENT SUPPORT

This invention was made with government support under Contract No. FA8721-05-C-0002 awarded by the U.S. Air Force. The Government has certain rights in this invention.

BACKGROUND OF THE INVENTION

In numerous situations, when explosive devices are prepared, transported, or otherwise handled, certain amounts of the explosive material end up on surfaces. Such surfaces may be clothing, a container, a vehicle, the ground, window sills, and so on. Failure to detect such materials on everyday items can result in concealed assembly and illegal transport of explosive materials and devices.

Explosives (unlike most other materials) generally are composed of a fuel and an oxidizer component. These will react under appropriate conditions (e.g., the addition of energy via heating or other means). An explosion requires that the combustion reaction occur at a rate such that shock waves are produced. Under alternative conditions, the reaction rate may be such that a release of the internal energy of the explosive, such as by combustion (oxidation of the fuel), occurs, but with no shock wave or explosion. In either case, the release of internal energy will have a measurable acoustic signature that can be used for detection.

Many detection methods have been used to detect explosives. Low intensity lasers have been used for photoacoustic spectroscopy (PAS), which detects a very weak acoustic signal caused by laser-induced sample heating. The heating and resultant acoustic signal are proportional to the material's absorption of energy. PAS is generally used to determine a material's absorption of energy as a function of laser wavelength, by identifying an explosive material from a comparison of the material's absorption of energy at a wavelength at which the explosive material is known to absorb energy, compared to the material's absorption of energy at a non-absorbing wavelength. PAS has had limited success in detecting explosives in realistic environments, because explosives lack sufficiently distinct absorption characteristics for low false alarm detection. PAS also requires probing a material with at least two laser wavelengths, as discussed above.

Most other explosive detection techniques use auxiliary properties (chemical or optical) of the explosives or their components for detection. For example, Raman-based detection detects scattered light whose wavelength shifts are related to the vibrational structure of the explosive molecules. One potential pitfall of such techniques is that similar properties (e.g., vibrational structure) may exist in other non-explosive materials, giving rise to false alarms. For example, X-ray transmission, X-ray backscatter, and THz imaging are sensitive only to bulk amounts of explosive materials or to metallic constituents in explosive devices. Ion-mobility spectrometry (IMS) requires surface sampling, for instance by airflow agitation, followed by collection of dislodged particles. Thus, the detection is relatively slow, and it is effective only at short distances (e.g., in a range of substantially less than about 1 meter). Raman spectroscopy has a very weak signature, requiring data collection for an extended period of time. Laser-induced breakdown spectroscopy (LIBS) is prone to generating false alarms in many situations, because it is largely non-specific, as it detects atomic constituents which are found in many compounds (oxygen and nitrogen). Differential reflectometry is effective only from relatively short distances (e.g., about 1 meter), and it is also prone to generating false alarms, because the signature that it relies on is complex and not well defined. Fluorescence quenching (e.g., the Fido™ detector by ICx Technologies, Arlington Va.) has some of the drawbacks of IMS discussed above: it requires that the molecules to be detected reach the detecting device in order to interact with a fluorescing polymer. The technique is therefore limited to stand-off distances in a range of less than about 1 meter.

Therefore, there is a need for a method of detecting explosives at a distance that minimizes or eliminates the above mentioned problems.

SUMMARY OF THE INVENTION

This invention generally is directed to stand-off detection of explosives.

In one embodiment, a method of detecting the presence of an explosive includes exposing a substrate to a pulsed focused energy source located at a target distance away from the substrate, the energy having a magnitude sufficient to release the internal energy of an explosive if present on the substrate and thereby generate an acoustic wave. The method also includes detecting the acoustic wave using a detector located at a detection distance away from the substrate. The detector can be a microphone or a laser vibrometer.

In another embodiment, a method of detecting the presence of an explosive includes exposing a substrate to a pulsed focused energy source located at a target distance away from the substrate, the energy having a magnitude sufficient to release internal energy of an explosive if present on the substrate and thereby generate a surface vibration on the substrate, and detecting the surface vibration using a detector located at a detection distance away from the substrate.

In yet another embodiment, a kit for detecting the presence of an explosive includes a pulsed focused energy source, the energy having a magnitude sufficient to release the internal energy of an explosive if present on a substrate located at a target distance away from the pulsed focused energy source and thereby generate an acoustic wave. The kit also includes a detector adapted to detect the acoustic wave at a detection distance away from the substrate.

This invention has many advantages including fast, stand-off, and specific detection of trace amounts of explosive materials with a single-wavelength focused energy source.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 is a schematic illustration of an apparatus for stand-off detection of trace amounts of explosive materials employing a microphone detector according to this invention.

DETAILED DESCRIPTION OF THE INVENTION

Figure 2A:
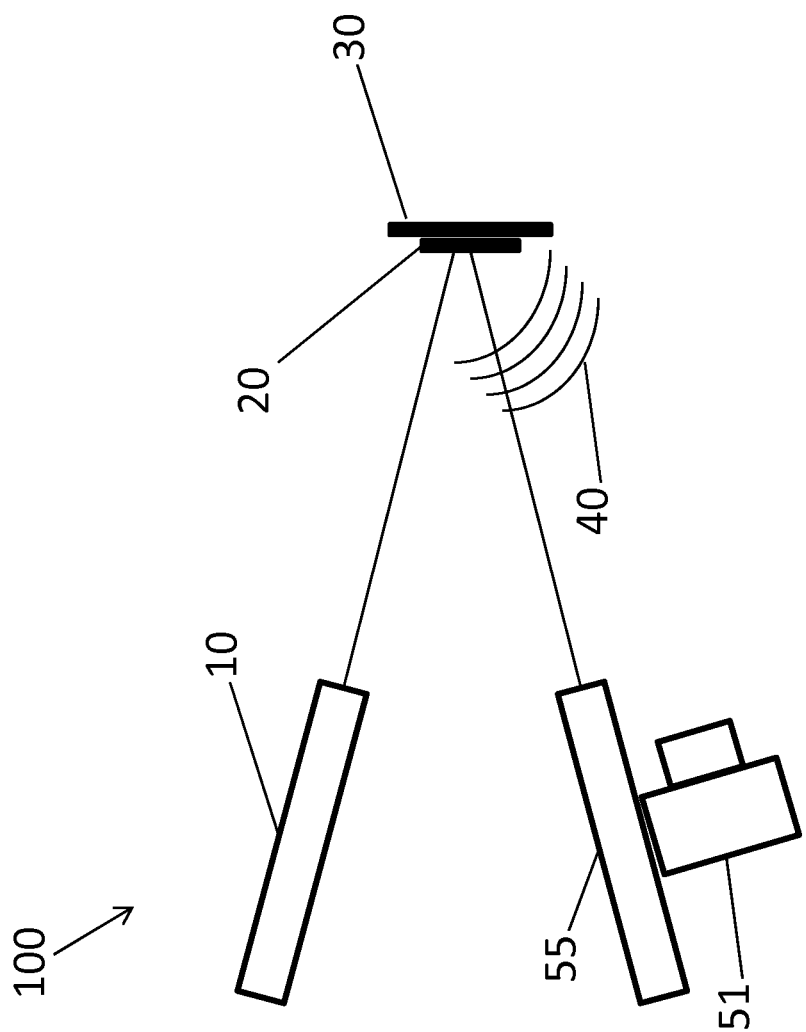
FIG. 2A is a schematic illustration of an apparatus for stand-off detection of trace amounts of explosive materials employing a laser vibrometer detector to illuminate the explosive according to this invention.

Stand-off detection of explosives is the ability to detect explosive residues from a distance by sampling a surface of, for example, an approaching vehicle, from a target distance, and detecting a signal from a detection distance. Explosive residues are perhaps the best indicator of concealed assembly or illegal transport of explosives. Rapid and early detection of dangerous explosive activity from a distance has many security applications, such as airport, building, venue, and military security.

In an embodiment shown in FIG. 1, kit 100 for detecting the presence of explosive 20 includes pulsed focused energy source 10 that can be located at a target distance away from substrate 30. The energy has a magnitude sufficient to release the internal energy of explosive 20 if present on substrate 30 and thereby generate acoustic wave 40. The energy magnitude can be in a range of between about 0.1 mJ/cm$^2$ and about 30 mJ/cm$^2$. Kit 100 also includes detector 50 adapted to detect acoustic wave 40 at a detection distance away from substrate 30. In some embodiments pulsed focused energy source 10 can be a pulsed laser, such as a laser having a pulse width in a range of between about 1 femtosecond and about 35 nanoseconds. The laser can be an ultraviolet laser, a visible laser, or an infrared laser. In a specific embodiment, the laser is a pulsed ultraviolet (UV) laser producing pulses of 250 nm wavelength light about 7 nanoseconds (ns) in duration.

Alternatively, the pulsed focused energy source can be a microwave energy source or a sonic energy source. The target distance can be in a range of between about 1 meter and about 1,000 meters. Detector 50 can be a microphone or a laser vibrometer, with a bandwidth equal to or greater than about 30 kHz. The detection bandwidth of the laser vibrometer can be equal to or greater than about 100 kHz. The detection distance can be in a range of between about 1 cm and about 1,000 meters.

Figure 2B:
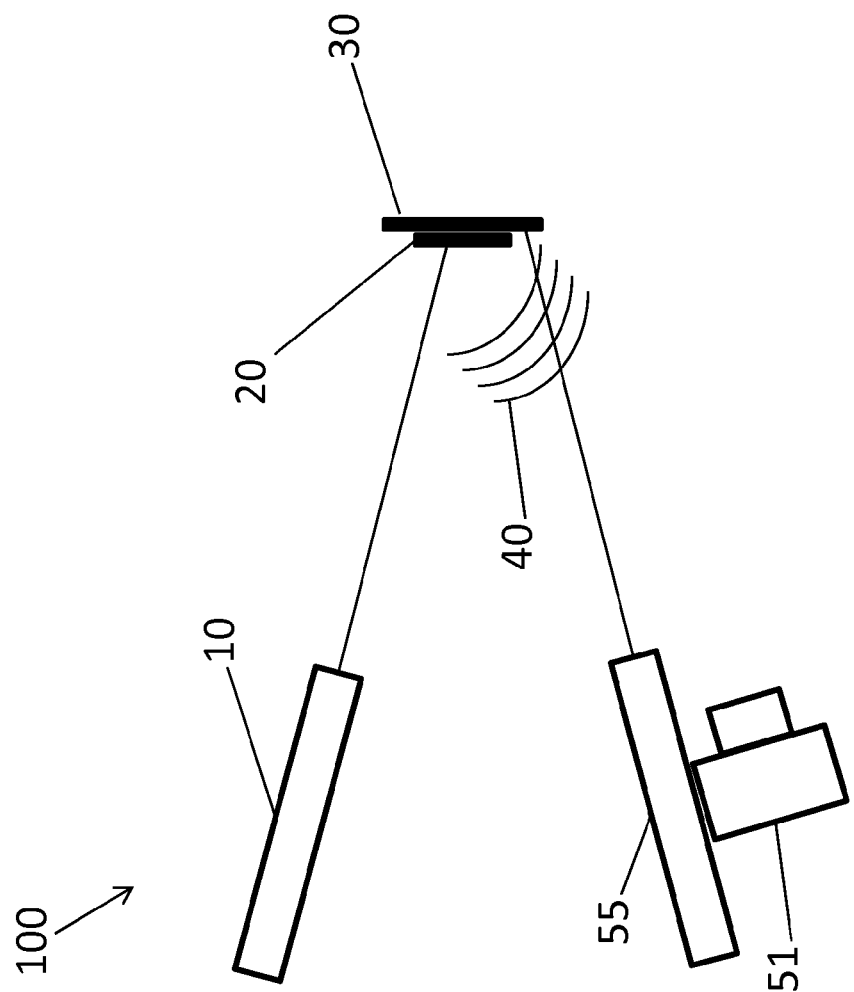
FIG. 2B is a schematic illustration of an apparatus for stand-off detection of trace amounts of explosive materials employing a laser vibrometer detector to illuminate the substrate according to this invention.

In the embodiment shown in FIG. 1, detector 50 can be a parabolic microphone that can detect acoustic wave 40 from a detection distance of up to about 20 meters. In another embodiment shown in FIGS. 2A and 2B, detector 51 can be a laser vibrometer that includes laser 55 and backscatter detector 51 that can be used to measure a surface vibration directly from the explosive 20, as shown in FIG. 2A, by modulating the laser carrier wave, and to measure the surface vibration in the air (acoustic wave 40) via a modulation of the laser carrier wave due to index of refraction changes from the surface vibration. Alternatively, as shown in FIG. 2B, laser 55 can be used to illuminate a nearby surface on substrate 30 and detector 51 can be used to detect only acoustic wave 40. Laser vibrometer detection is estimated to enable a detection distance on the order of about 1,000 meters and detection from a moving platform, such as a ground or airborne vehicle.

In another embodiment, a laser vibrometer can be used to measure ablation phenomena caused by the pulsed laser, such as vaporization, chipping, or erosion of the targeted material surface, or other local motion related to the energy release. In yet other embodiments, other processes include adjusting the pulse repetition frequency (PRF) of the pulsed laser to induce lower frequency vibrations and resonances in the target via ablation processes.

Turning back to FIG. 1, a method of detecting the presence of explosive 20 includes exposing substrate 30 to pulsed focused energy source 10 located at a target distance away from substrate 30, the energy having a magnitude sufficient to release the internal energy of explosive 20 if present on substrate 30 and thereby generate acoustic wave 40. The method also includes detecting acoustic wave 40 using detector 50 located at a detection distance away from substrate 30.

Exemplification

Figure 3:
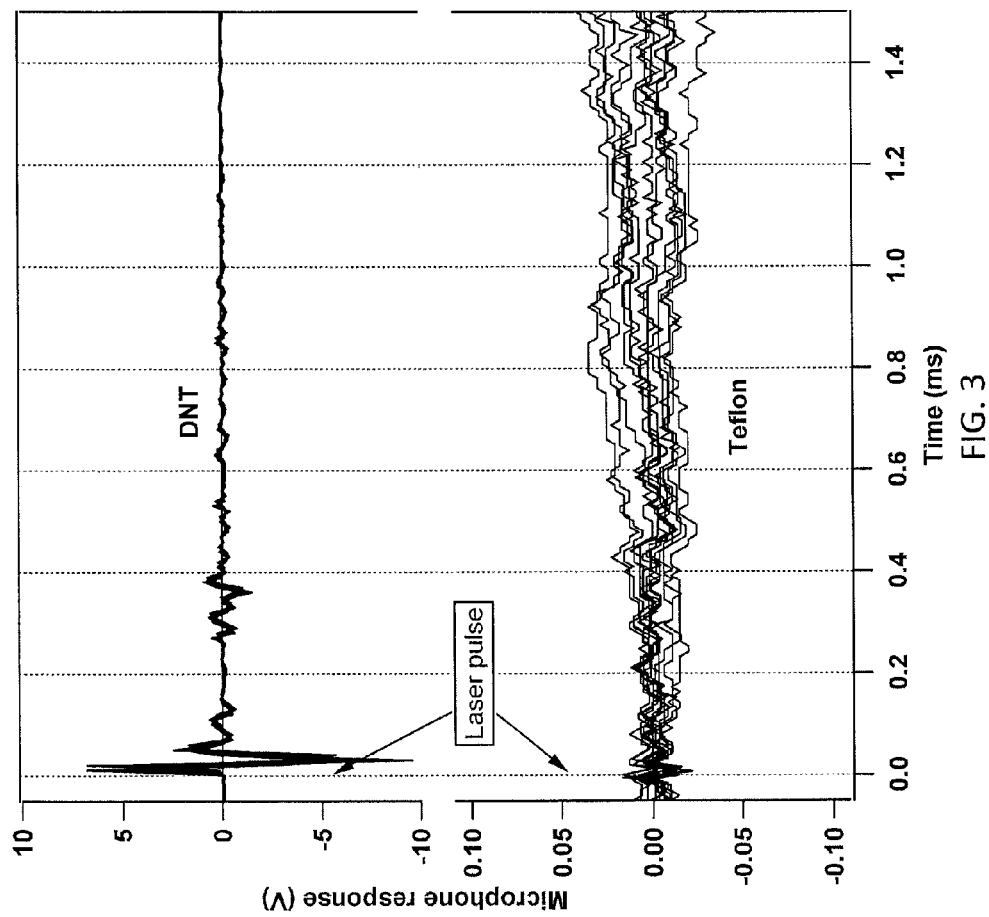
FIG. 3 is a graph of photo-induced acoustic response to a laser pulse as a function of time for various materials. The laser pulse is indicated by arrows. Note that Teflon had no measurable acoustic signal, comparable to the signal obtained from experiments with most non-explosive materials.

Laboratory studies of the signal strength were performed with dinitrotoluene (DNT), trinitrotoluene (TNT), and RDX (hexahydro-1,3,5-trinitro-1,3,5-triazine, the explosive component of C4 plastic explosive). The TNT sample was a trace residue, while the other explosives were bulk amounts (>mg). The noise-limited detection sensitivity for TNT was about 100 ng/cm$^2$. Numerous non-explosive materials such as plastics (e.g., Teflon, Plexiglass), cloths, (e.g., cotton), metals, (e.g., aluminum), ceramics, sugar, fertilizer, paper, and water were also tested. A pulsed UV (250 nm) laser (Continuum 9030, Continuum Inc., Santa Clara, Calif.) was focused onto the samples. The 250 nm laser pulses were about 7 ns in duration with a fluence at target of about 15 mJ/cm$^2$. The acoustic detector was a microphone (Earthworks M30 HDM, Milford, N.H.) with a response that decreased beyond 30 kHz, which was positioned at a detection distance of about 4 inches from the samples. Typical acoustic responses are shown in FIG. 3.

Figure 4:
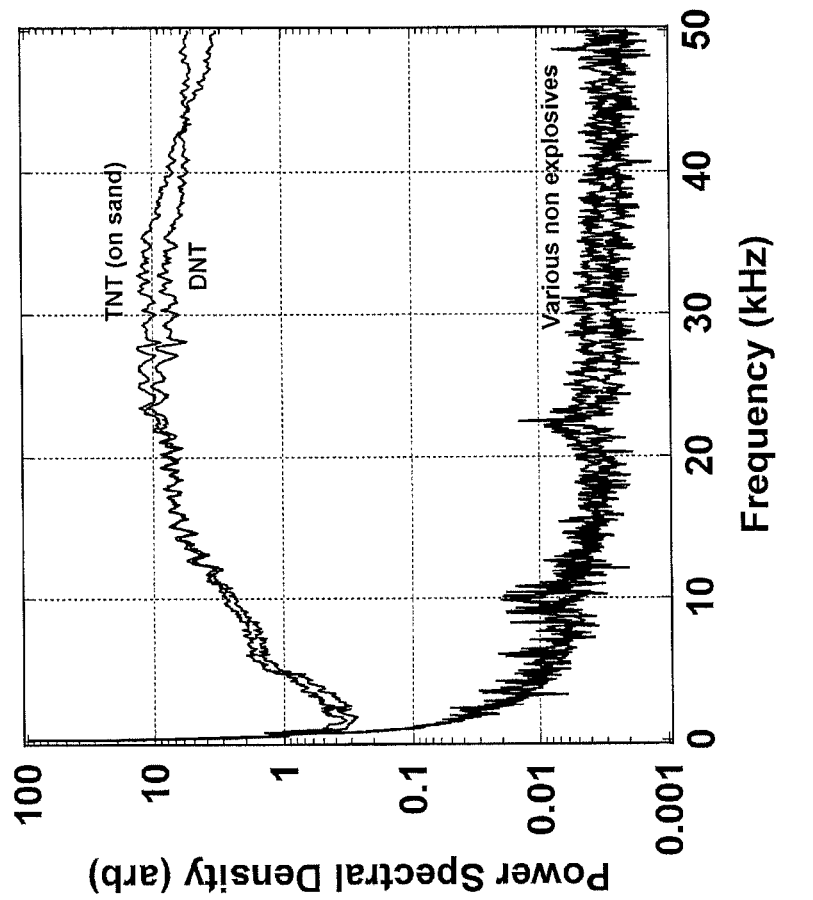
FIG. 4 is a graph of power spectral density as a function of frequency (kHz) for photo-induced acoustic signals. The power spectral density signals of various non-explosive materials were nearly indistinguishable from one another. The non-explosive materials included Teflon, aluminum, cotton, sugar, fertilizer and Plexiglas. Signals are averages over 15 successive laser pulses.
Figure 5:
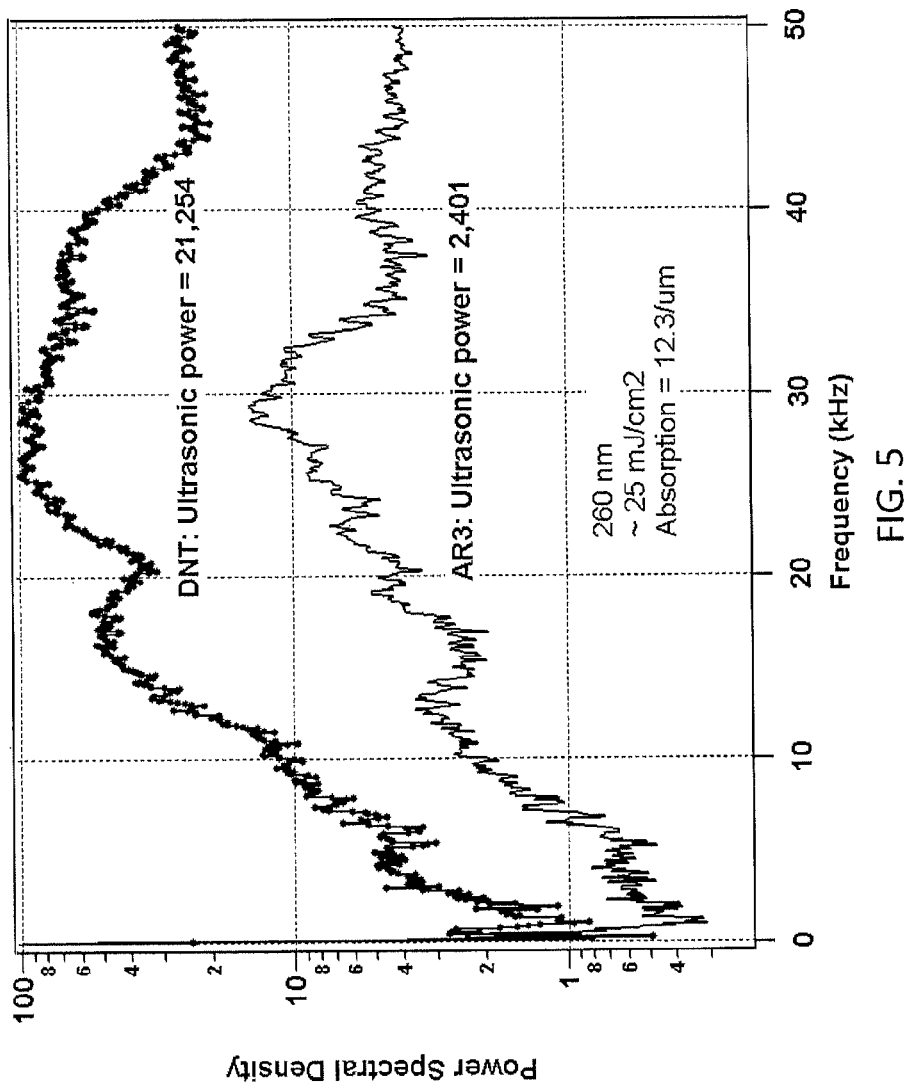
FIG. 5 is a graph of power spectral density as a function of frequency (kHz) for photo-induced acoustic signals of DNT and AR3, a non-explosive coating material.

A significant signal was observed from DNT, RDX, and TNT. As shown in FIG. 3, the majority of the acoustic signal was contained in a very short pulse, the width of which was on the order of 10 μs. Numerous non-explosive materials such as plastics (e.g., Teflon, Plexiglass), cloths, (e.g., cotton), metals, (e.g., aluminum), ceramics, sugar, fertilizer, paper, and water were probed and showed no measureable acoustic signal, as shown in FIG. 4. To confirm that absorptive heating was not the dominant cause of the acoustic signal observed (as would be the case in traditional PAS), an optically thick (about 1 μm) solid film of AR3 (an optical coating made by Shipley, Marlborough, Mass.) on a glass substrate. The optical absorption spectra of the AR3 and a similar solid film of DNT were measured. At 260 nm, both materials had an absorption intensity of 12.3 μm$^{-1}$. Photoacoustic measurements of DNT and AR3 were made using a 260 nm laser. As shown in FIG. 5, the photoacoustic response of DNT was about nine times stronger, indicating that simple absorptive heating is not the dominant cause of the measured acoustic signal of DNT. Furthermore, the energy efficiency of the photoacoustic process was estimated. The ratio of acoustic energy output to optical energy output is estimated to be at least 5×10$^{-6}$ (estimated assuming that the microphone was lossless, despite the known attenuation of the microphone response at these detection frequencies). This efficiency result is several orders of magnitude larger than the typical efficiency due to absorptive heating measured by PAS, where the typical efficiency for absorptive heating processes is in a range of between about $10^{-8}$ and about $10^{-12}$. See A. C. Tam, *Applications of photoacoustic sensing techniques*, Rev. Mod. Phys. 56, p. 381 (1986).

Spectral analysis using a standard fast Fourier transform (FFT) algorithm of the acoustic signals detected by microphone is shown in FIG. 4. The resultant power spectral density (PSD) was averaged over 15 successive laser pulses. As shown in FIG. 4, explosive materials such as DNT and TNT showed a much larger signal than various non-explosive materials such as plastics (e.g., Teflon, Plexiglass), cloths, (e.g., cotton), metals, (e.g., aluminum), ceramics, sugar, fertilizer, paper, and water also shown collectively in FIG. 4 labeled as "Various non-explosives." Since ambient acoustic noise is typically quite low in the ultrasonic region above 25 kHz, and there is appreciable acoustic power detected from explosives at these frequencies and above, this high frequency region would be an ideal portion of the acoustic spectrum in which to detect explosives.

Figure 6:
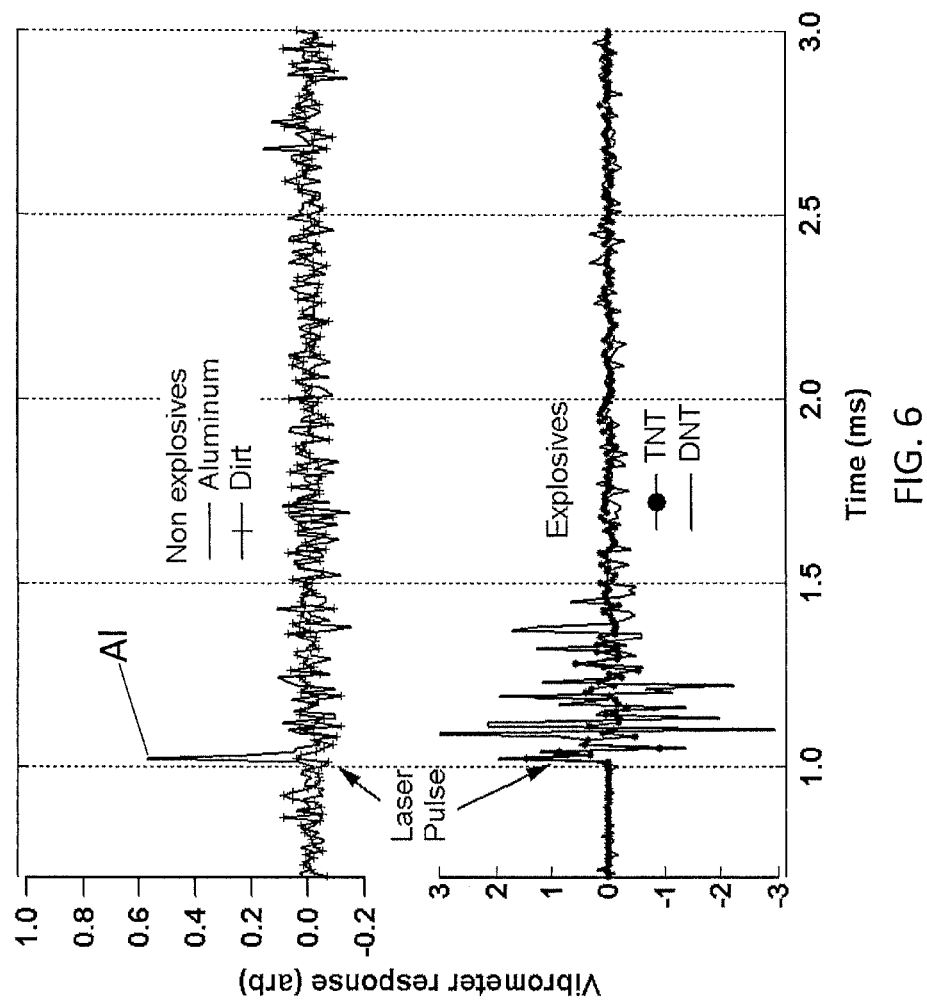
FIG. 6 is a graph of photo-induced vibrometer response to a laser pulse as a function of time for various materials. The laser pulse is indicated by arrows.

FIG. 6 shows the response as a function of time of a laser vibrometer (Polytec OFV-505, Polytec Inc., Irvine, Calif.) operated as shown in FIG. 2A, that is, with laser 55 illuminating the target surface. As shown in FIG. 6, there was almost no measurable response from dirt, and a response lasting about as long as the laser pulse was detected from an aluminum surface, as compared to the signal detected from explosives such as TNT and DNT that lasted substantially longer, about 500 microseconds.

Figure 7:
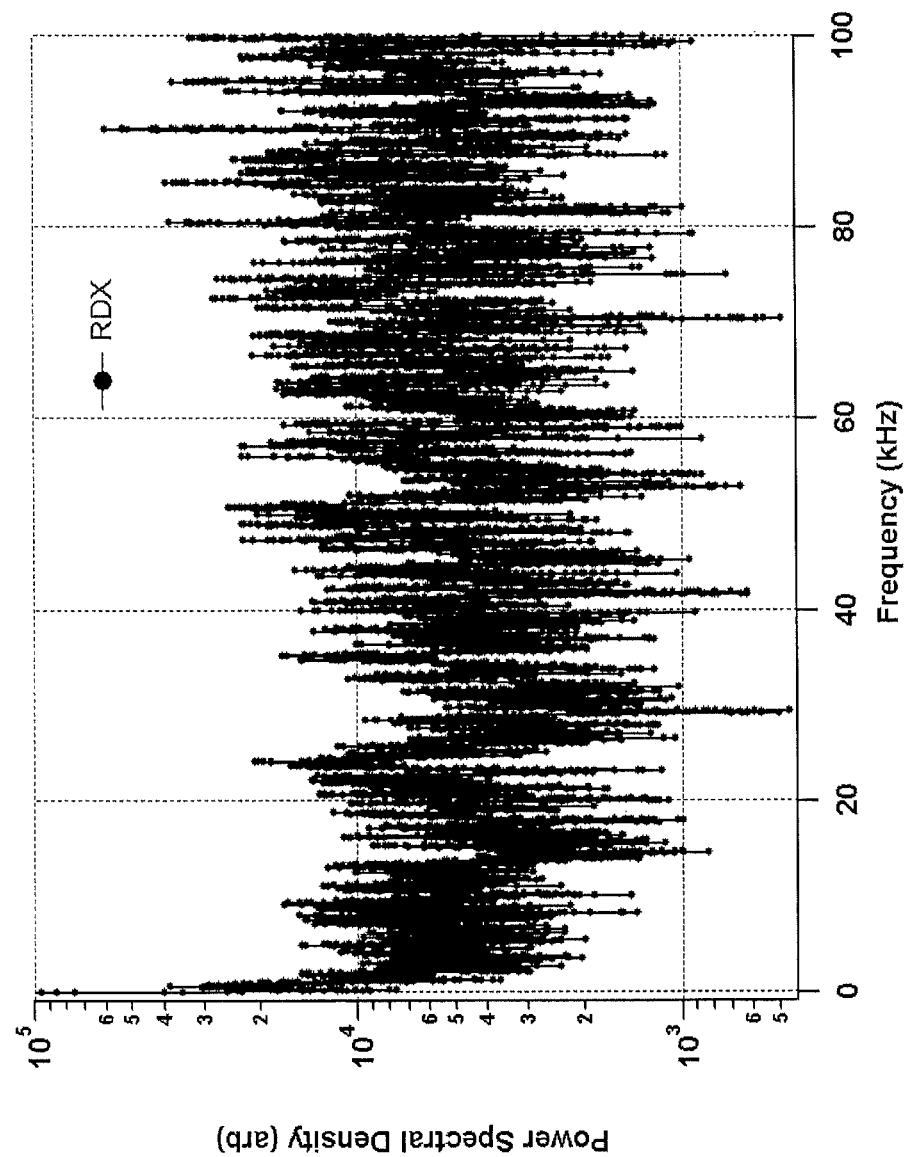
FIG. 7 is a graph of power spectral density as a function of frequency (kHz) for a photo-induced vibrometer signal of RDX.

Spectral analysis of the signals detected by laser vibrometer from the explosive RDX is shown in FIG. 7. There is substantial signal detected up to about 100 kHz, which was the resolution of the system. Measurements of TNT and DNT produced almost the same results, while measurements of non-explosives are expected to yield a signal about 1000 times weaker.

Incorporation by Reference

The teachings of all patents, published applications and references cited herein are incorporated by reference in their entirety.

Equivalents

While this invention has been particularly shown and described with references to example embodiments thereof, it will be understood by those skilled in the art that various changes in form and details may be made therein without departing from the scope of the invention encompassed by the appended claims.

What is claimed is:

1. A method of detecting the presence of an explosive, comprising:
   a) exposing a substrate to a pulsed laser energy source wherein the pulse has a width in a range of between about 1 femtosecond and about 35 nanoseconds, and wherein the energy source has a magnitude in a range of between about 0.1 mJ/cm² and about 30 mJ/cm², sufficient to release internal energy of an explosive if present on the substrate and thereby generate an acoustic wave; and
   b) detecting the acoustic wave using a detector.

2. The method of claim 1, wherein the laser is an ultraviolet laser.

3. The method of claim 1, wherein the laser is a visible laser.

4. The method of claim 1, wherein the laser is an infrared laser.

5. The method of claim 1, wherein the detector is a microphone.

6. The method of claim 1, wherein the detector is a laser vibrometer.

7. The method of claim 1, wherein the acoustic wave is detected at a distance in a range of between about 1 cm and about 1,000 meters.

8. A method of detecting the presence of an explosive, comprising:
   a) exposing a substrate to a pulsed laser energy source, wherein the pulse has a width in a range of between about 1 femtosecond and about 35 nanoseconds, the energy having a magnitude in a range of between about 0.1 mJ/cm² and about 30 mJ/cm², sufficient to release internal energy of an explosive if present on the substrate and thereby generate a surface vibration on the substrate; and
   b) detecting the surface vibration using a detector.

9. The method of claim 8, wherein the laser is an ultraviolet laser.

10. The method of claim 8, wherein the laser is a visible laser.

11. The method of claim 8, wherein the laser is an infrared laser.

12. The method of claim 8, wherein the detector is a laser vibrometer.

13. The method of claim 8, wherein the detection acoustic wave is detected at a distance in a range of between about 1 cm and about 1,000 meters.

14. A kit for detecting the presence of an explosive comprising:
   a) a pulsed laser energy source, the pulse of energy source having a width in a range of between about 1 femtosecond and about 35 nanoseconds, wherein the energy source has a magnitude in a range of between about 0.1 mJ/cm² and about 30 mJ/cm²,sufficient to release internal energy of an explosive if present on a substrate and thereby generate an acoustic wave; and
   b) a detector adapted to detect the acoustic wave.

15. The kit of claim 14, wherein the laser is an ultraviolet laser.

16. The kit of claim 14, wherein the laser is a visible laser.

17. The kit of claim 14, wherein the laser is an infrared laser.

18. The kit of claim 14, wherein the detector is a microphone.

19. The kit of claim 14, wherein the detector is a laser vibrometer.

* * * * *

UNITED STATES PATENT AND TRADEMARK OFFICE
CERTIFICATE OF CORRECTION

PATENT NO. : 8,935,960 B2  
APPLICATION NO. : 13/010333  
DATED : January 20, 2015  
INVENTOR(S) : Charles M. Wynn et al.

It is certified that error appears in the above-identified patent and that said Letters Patent is hereby corrected as shown below:

In the Claims

In Column 6, Claim 13, Line 36 delete "detection".

Signed and Sealed this
Twelfth Day of May, 2015

Michelle K. Lee
*Director of the United States Patent and Trademark Office*